Figure 1:
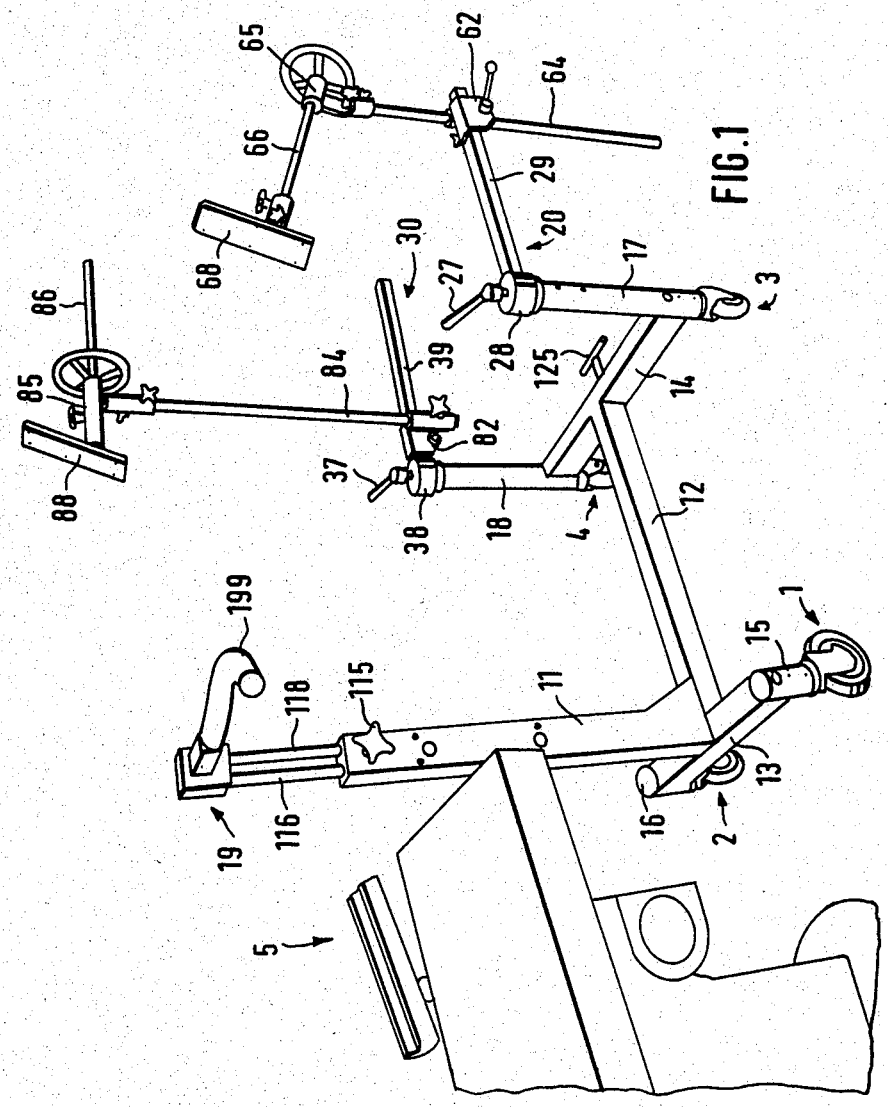

United States Patent [19]

Ruf

[11] Patent Number: 4,527,555

[45] Date of Patent: Jul. 9, 1985

[54] AUXILIARY TABLE FOR EXTENSION AND REPOSITIONING IN MEDICAL OPERATIONS

[76] Inventor: Hermann Ruf, Pfützenstr. 58, 6103 Griesheim, Fed. Rep. of Germany

[21] Appl. No.: 621,144

[22] Filed: Jun. 18, 1984

Related U.S. Application Data

[63] Continuation of Ser. No. 379,452, May 18, 1982, abandoned.

[30] Foreign Application Priority Data

May 18, 1981 [DE] Fed. Rep. of Germany ... 8114666[U]
May 19, 1981 [DE] Fed. Rep. of Germany ....... 3119900

[51] Int. Cl.³ .............................................. A61F 5/00
[52] U.S. Cl. ...................................... 128/69; 269/322
[58] Field of Search ..................... 128/69, 70, 71, 83, 128/84 R, 84 B, 68; 269/322, 325, 326, 328

[56] References Cited

U.S. PATENT DOCUMENTS

| | | |
|---|---|---|
| 848,137 | 3/1907 | Hubbell . |
| 1,501,120 | 7/1924 | Karrer . |
| 3,135,257 | 6/1964 | Anderson . |
| 3,654,920 | 4/1972 | Staib . |
| 3,745,996 | 7/1973 | Rush, Sr. . |

FOREIGN PATENT DOCUMENTS

| | | |
|---|---|---|
| 742951 | 12/1943 | Fed. Rep. of Germany . |
| 7805301 | 7/1978 | Fed. Rep. of Germany . |
| 1319436 | of 1963 | France . |
| 1427080 | of 1966 | France . |
| 435995 | 9/1935 | United Kingdom . |

OTHER PUBLICATIONS

B. Kohler and G. Scheuba, "Verriegelungsnagelung", Feb. 1978, pp. 21–24.

Primary Examiner—John D. Yasko
Attorney, Agent, or Firm—Andrus, Sceales, Starke & Sawall

[57] ABSTRACT

The invention relates to an auxiliary table for operations for the extension and repositioning of an extremity in preparation for the nailing of bones or the like. The table has a frame movable on rollers, that has a longitudinal member with a proximal and a distal transverse beam. A mount is fastened on the proximal transverse beam. On the distal transverse beam, two pivotable arms with adjustable extension rods are mounted. In order to make possible free access to the location of the fracture by the operator and the video recording apparatus, the mount (19) is vertically movably supported on a free-standing support column (11) integral with the frame (12, 13, 14). Free-standing posts (17, 18) are fastened on the lateral ends of the distal transverse beam (14) of the frame on which arms (20, 30) are supported.

42 Claims, 30 Drawing Figures

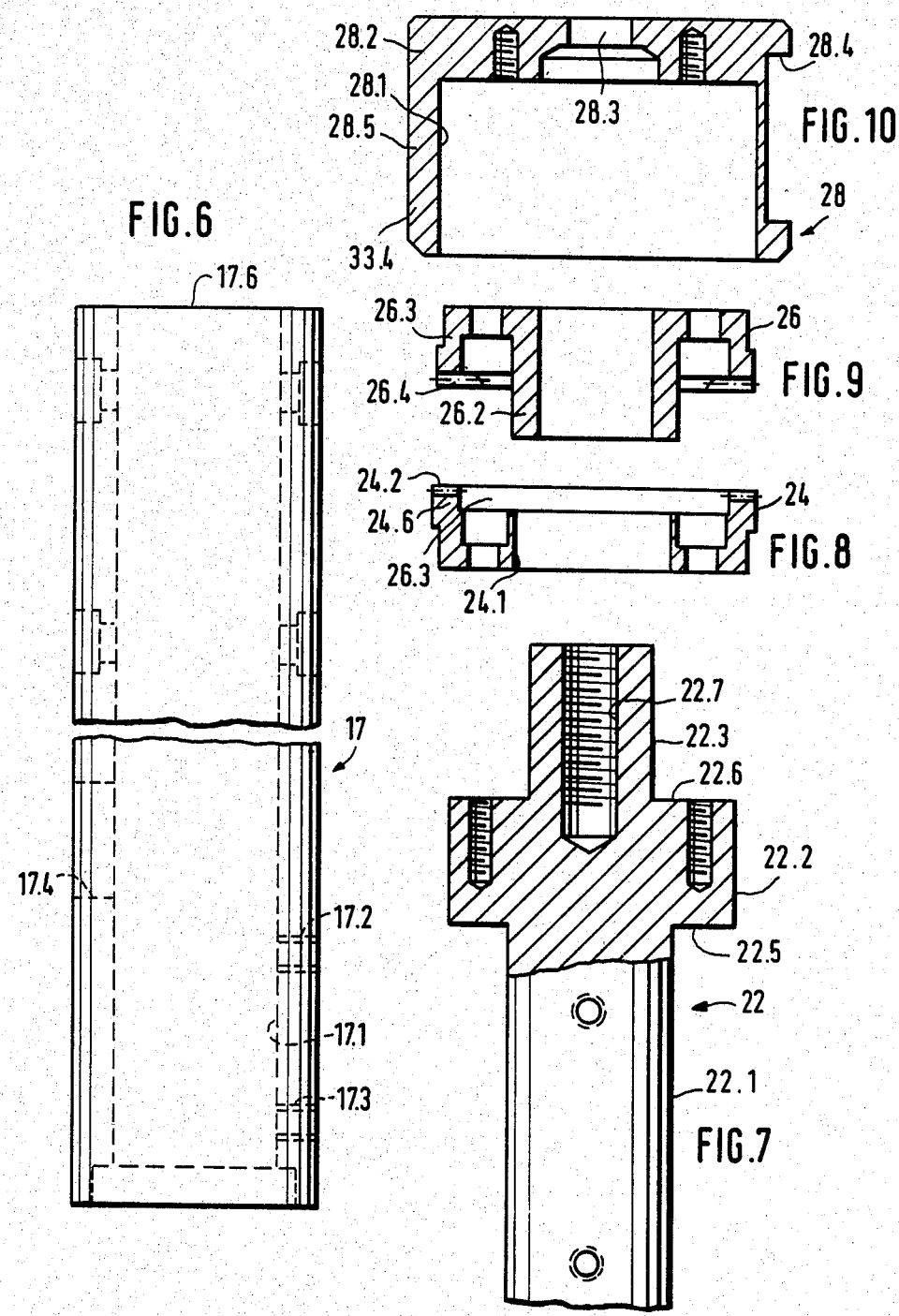

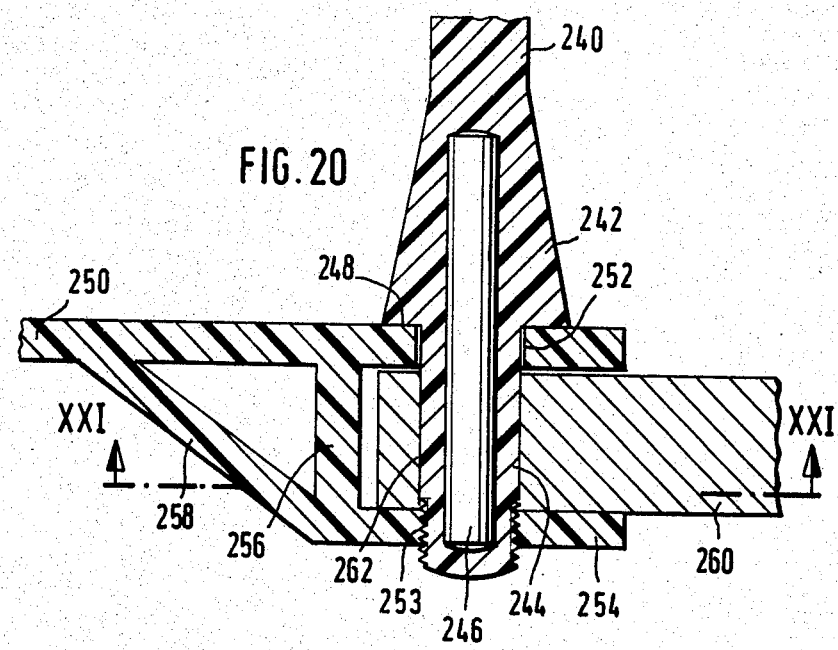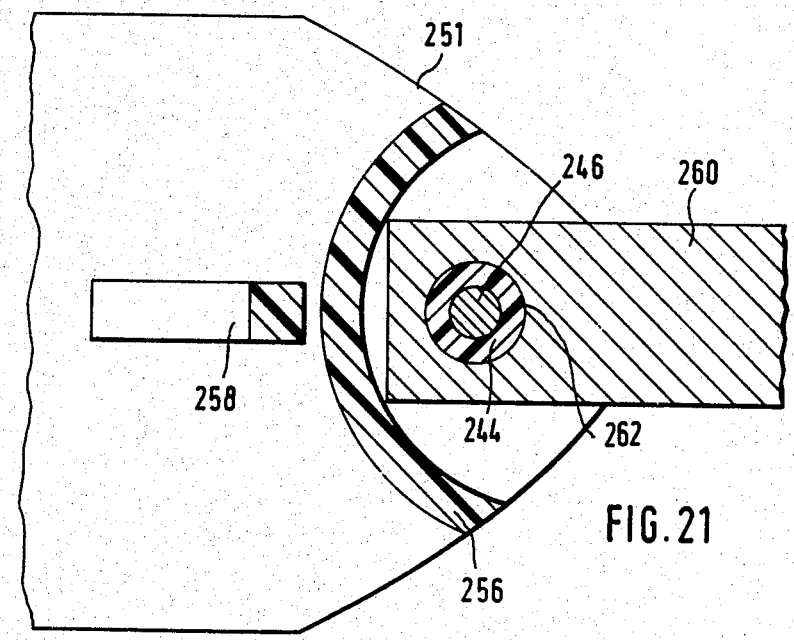

AUXILIARY TABLE FOR EXTENSION AND REPOSITIONING IN MEDICAL OPERATIONS

This application is a continuation of Ser. No. 379,452 filed May 18, 1982 now abandoned.

The invention relates to an auxiliary table for the extension and repositioning of an extremity in a medical operation in preparation for the pinning of bones or the like. The table has a frame movable on rollers, that has a longitudinal member with a proximal and a distal transverse beam. A mount is fastened on the proximal transverse beam. On the distal transverse beam, two pivotable arms with adjustable extension rods are fastened.

An auxiliary table of this type has been introduced as a WITTMOSER-Table by B. Koehler and G. Scheuba at a symposium in February, 1978 in Vienna and has been described by V. Vecsei in "Verriegelungsnagelung", 1978, pages 21 through 24. On a member connecting two stanchion heads, two vertical and laterally movable supports are displaceable in the longitudinal direction of the auxiliary table and the working height can be varied through motorized operation of the stanchions. The proximal stanchion carries two spaced vertically extendable supports, which carry the mount. On the head of the distal stanchion, two arms are independently pivotally hinged, on which the extension rods are adjustably fastened.

This auxiliary table is to be sure an indispensable aid for the pinning of bones; however its use at present is awkward. For the locking of the nails, the supports must frequently be dissassembled, as they impair the work field of the operator. Further, the links, particularly on the stanchions of the auxiliary table, can be maintained clean only with difficulty so that sanitary problems often arise.

The object of the present invention lies in the provision of a table auxiliary to the operating table for extension and repositioning, which, with the retention of full functional efficiency, does not obscure the work field of the operator and permits a free access to the location of the fracture both for the operator, as well as for the video recording apparatus.

To this end, the invention provides in the above noted auxiliary operation table, that the mount is vertically movably supported on a free-standing proximal support column integrally connected with the frame and that on the lateral ends of each of the distal transverse beams of the frame, a free-standing post is fastened, on which is supported one of the arms. Except for a U-formed element combining the support column and the member connecting one or the other posts, in the intermediate area between the support column and posts, unhindered accessibility both for the operator as well as the C-formed mountings of the recording camera is permitted. As the connection line of the support column to each of the two posts does not lie parallel to the longitudinal member, the auxiliary table according to the invention can also be employed non-axially to the operation table. This is advantageous for many occasions of use. Further, the wide spacing of the posts from each other is advantageous for the final pinning. Finally, the free space provided between the support column and posts permits the coupling of a repositioning device, such as the repositioning mount according to the invention.

The repositioning mount has its own carriage that moves under the longitudinal member for being coupled therewith. According to the invention, an auxiliary table central locking, preferably provided in the longitudinal member and the transverse beams thereof, permits the auxiliary table either with or without the repositioning mount to be precisely locked or released through a single lever operation.

The coupled repositioning mount carries on a narrow table two supports displaceable in the longitudinal direction of the table, each of which can be adjusted independently laterally and in height. Also, the table can, in its entirety, through single hand operation be raised or lowered with the already adjusted supports, as may be desired for the production of a Valgus-positioning or Varus-positioning. This height adjustment occurs, in accordance with the invention, independently from the other settings on the extension rods or on the mount of the auxiliary table according to the invention.

The sterility of the auxiliary table according to the invention causes no problem, as the functional aspects of the table according to the invention are assured without lubrication, readjustment or maintenance. The maintenance free supports, in particular, of the arms and the mount, are so encapsulated, that dirt cannot penetrate and the auxiliary table can be easily cleaned.

The features of the auxiliary table according to the invention are fully defined in the appended claims.

Figure 2:
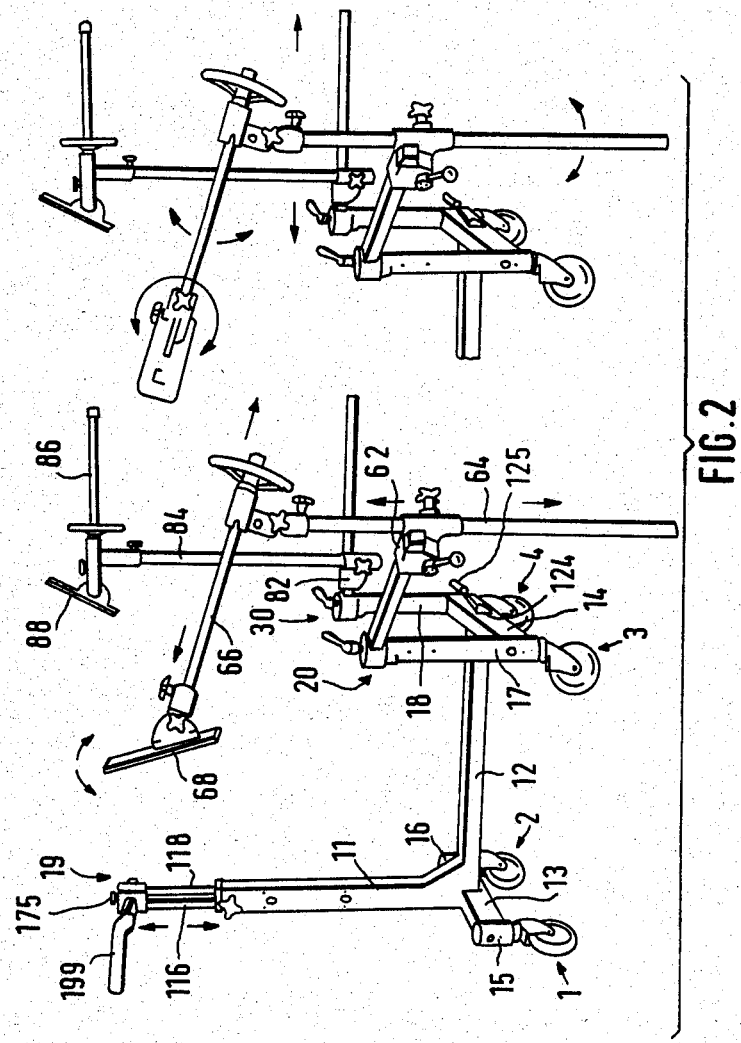
Figure 3:
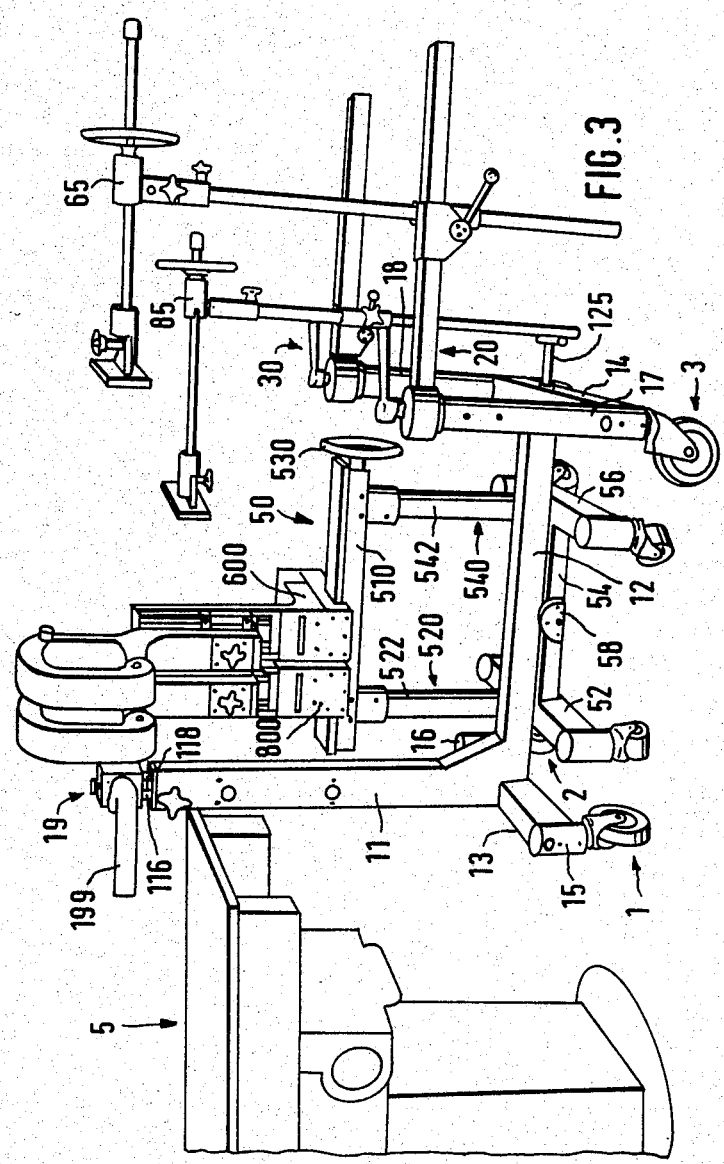
Figure 4:
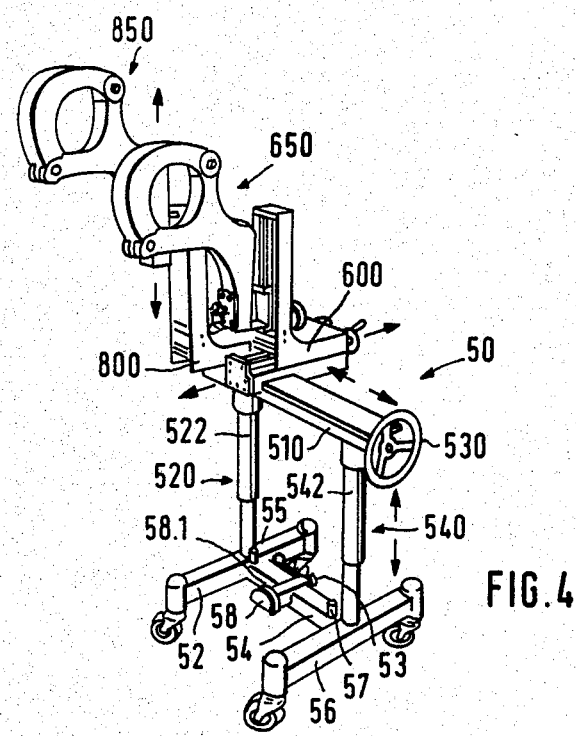
Figure 5:
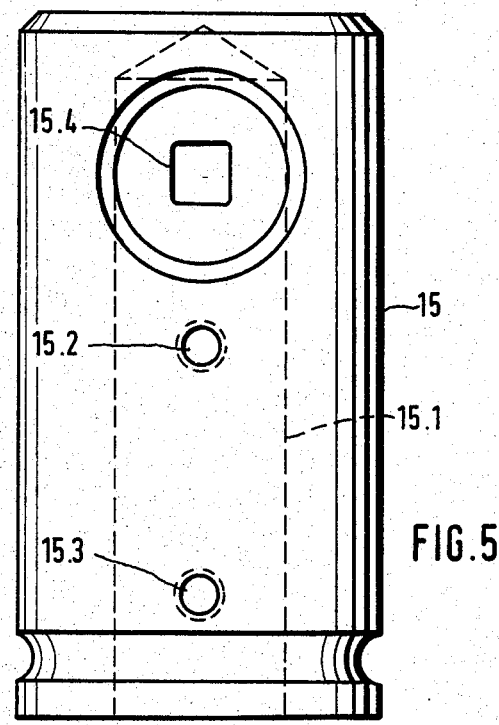
Figure 11:
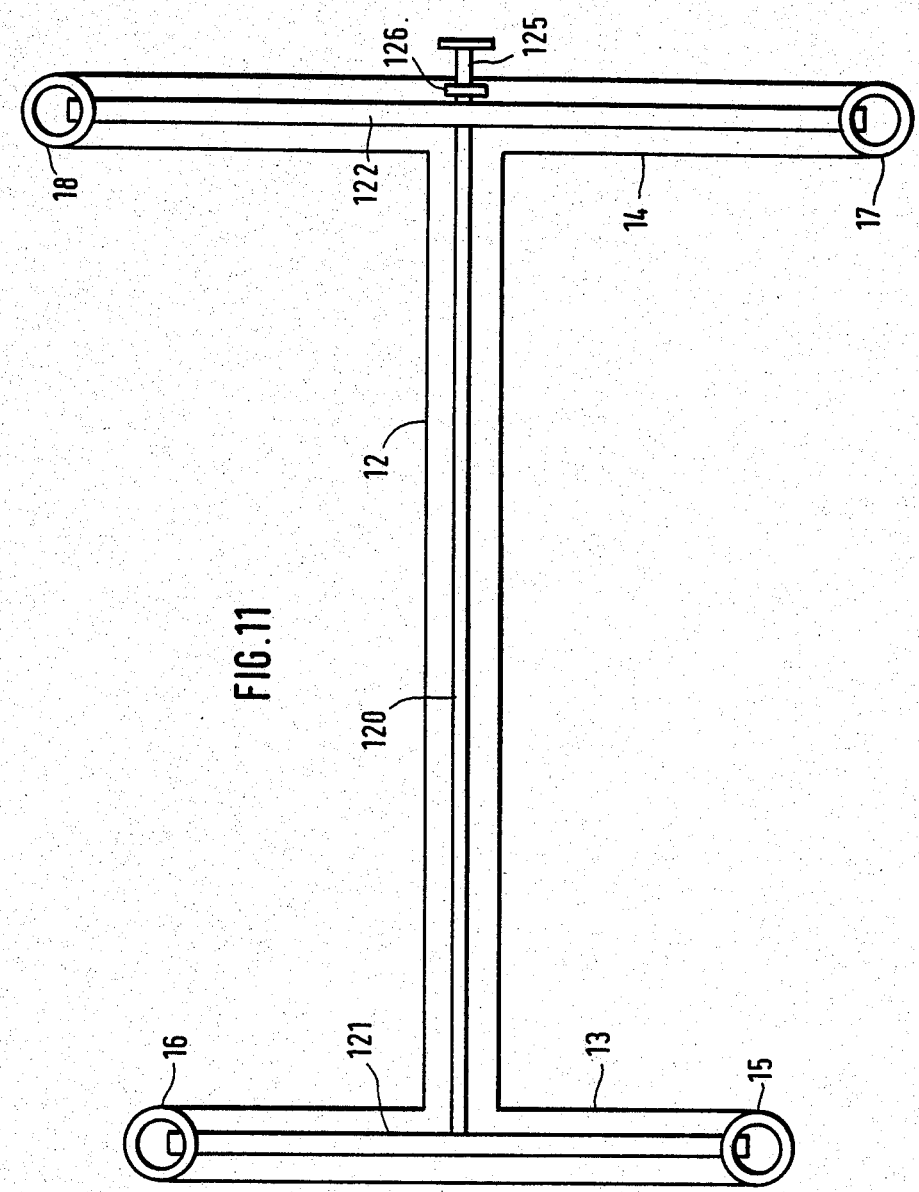
Figure 12:
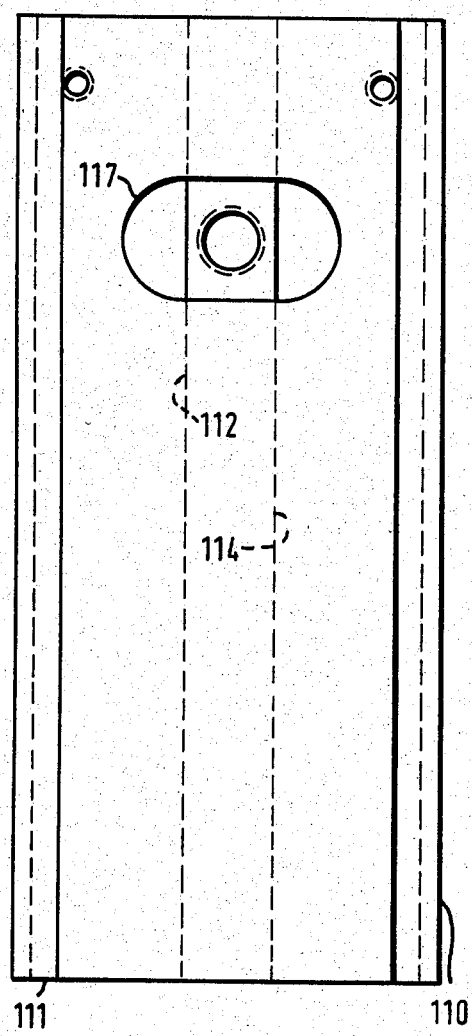
Figure 14:
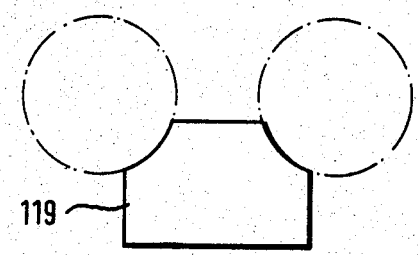
Figure 15:
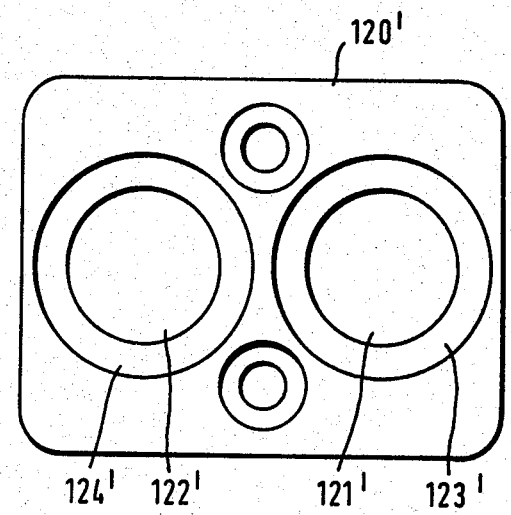
Figure 13:
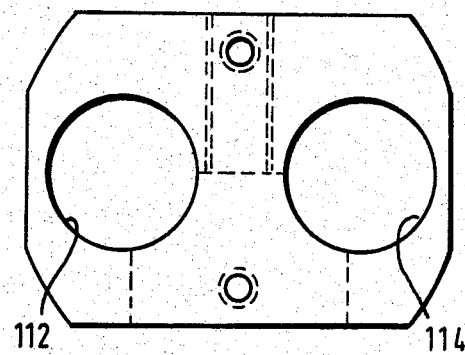
Figure 16:
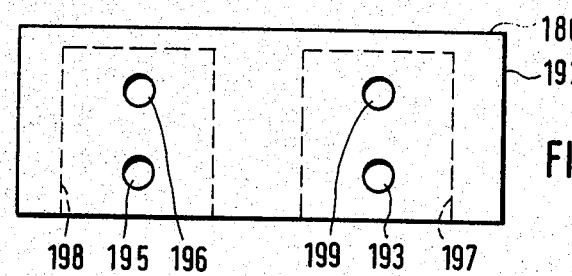
Figure 17:
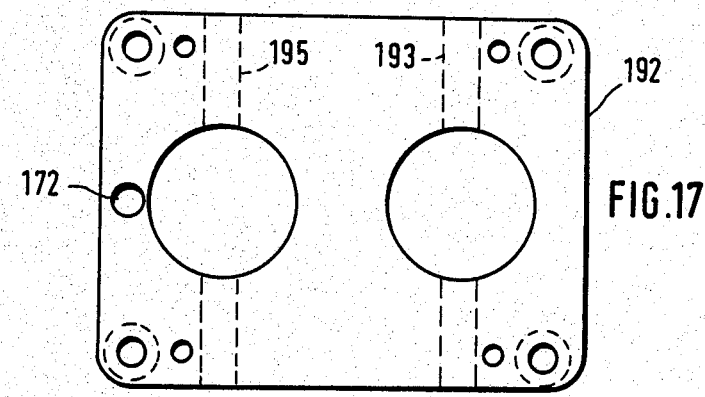
Figure 18:
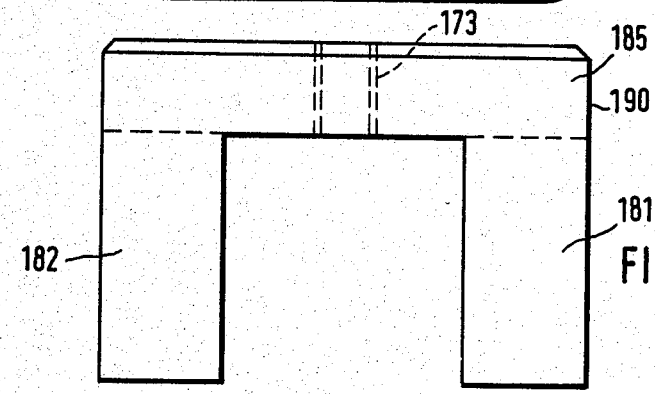
Figure 19:
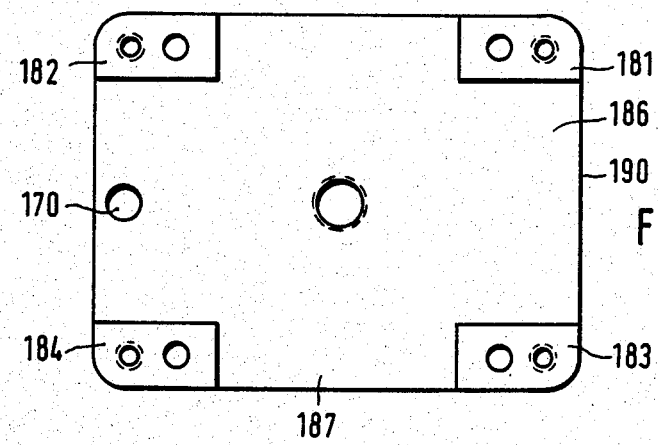
Figure 22:
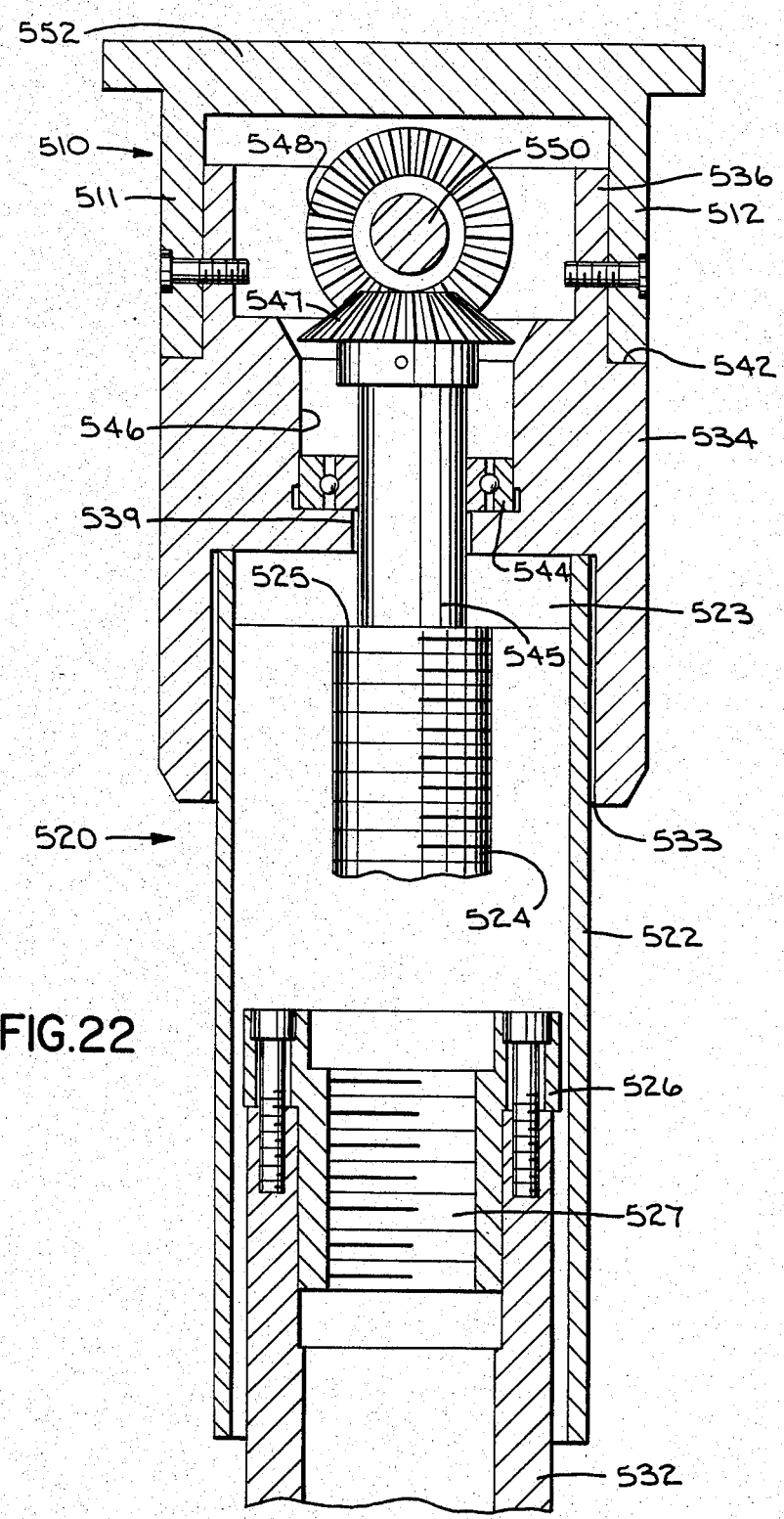

The invention is described in detail below with the aid of exemplary embodiments disclosed in the attached drawings. The drawings show:

FIG. 1—a perspective view of the auxiliary table according to the invention in association with an operating table;

FIG. 2—a schematic perspective view of the auxiliary table illustrating the different degrees of freedom of the mount and the extension rods in the auxiliary table according to the invention;

FIG. 3—a perspective view of the auxiliary table according to FIG. 1 with a coupled repositioning mount;

FIG. 4—a schematic perspective view of the reposition mount according to the invention with supports and the vertical adjustability of the support table;

FIG. 5—an elevational view of a foot of the proximal transverse beam;

FIG. 6—an elevational view of a post on one of the lateral ends of the distal transverse beam;

FIGS. 7–10—a partially cut away view of the insert, as well as the lower and upper locking discs and the arm head for the posts according to FIG. 6;

FIG. 11—a schematic representation of the linkage bars of the central locking;

FIGS. 12 and 13—an elevational view and plan view of the bushing in the support column 11;

FIG. 14—a schematic representation of the action of the locking brake for the height adjustment of the mount;

FIG. 15—a plan view of the sealing plate of the support column 11;

FIGS. 16 and 17—a side view and under side plan view of the head plate for the mount-guide rods;

FIGS. 18 and 19—a side view as well as a view from beneath of the mounting head;

FIG. 20—a view of a vertical section through the supporting plate and its fastening;

FIG. 21—a representation of a view from beneath of the apparatus of FIG. 20 cut along the lines XXI—XXI of FIG. 20;

FIG. 22—a schematic representation of a lifting cylinder for the repositioning mount.

Figure 23:
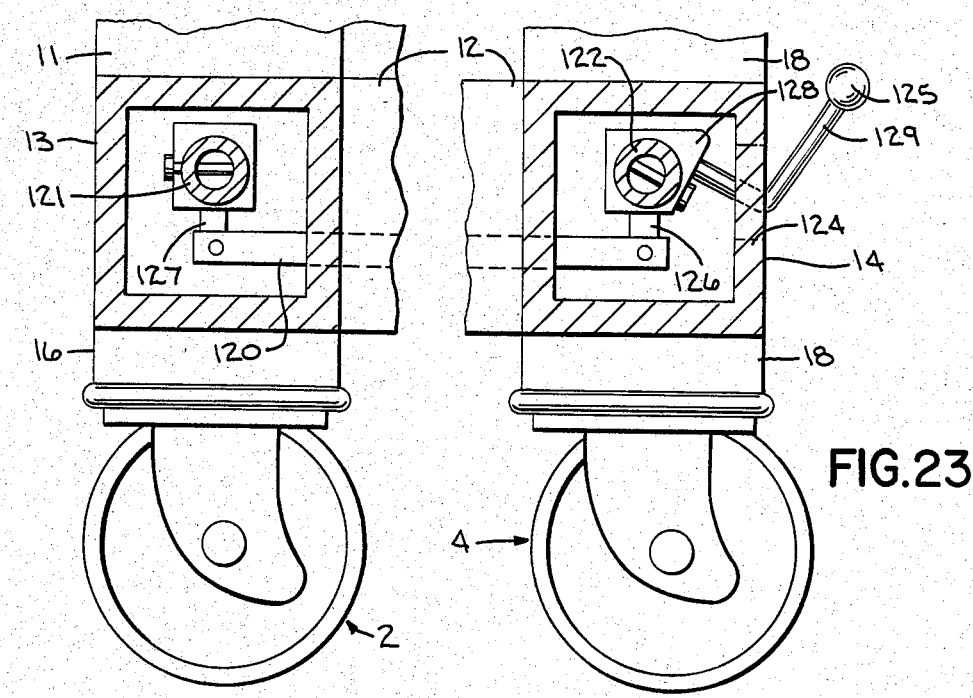
Figure 30:
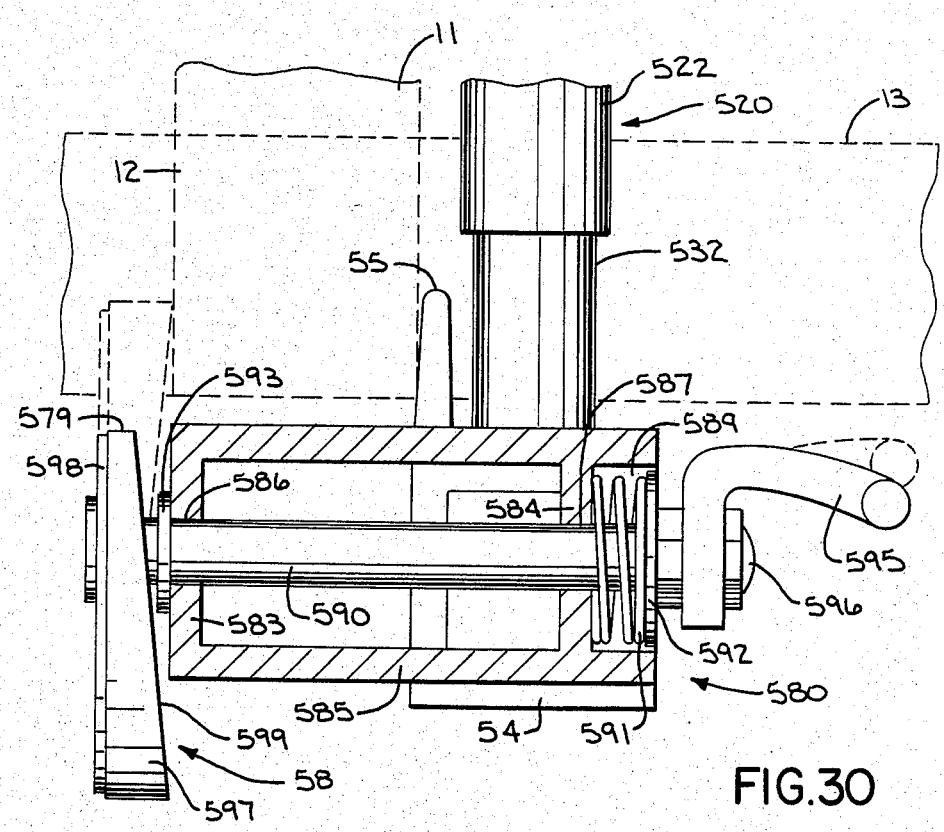
Figure 24:
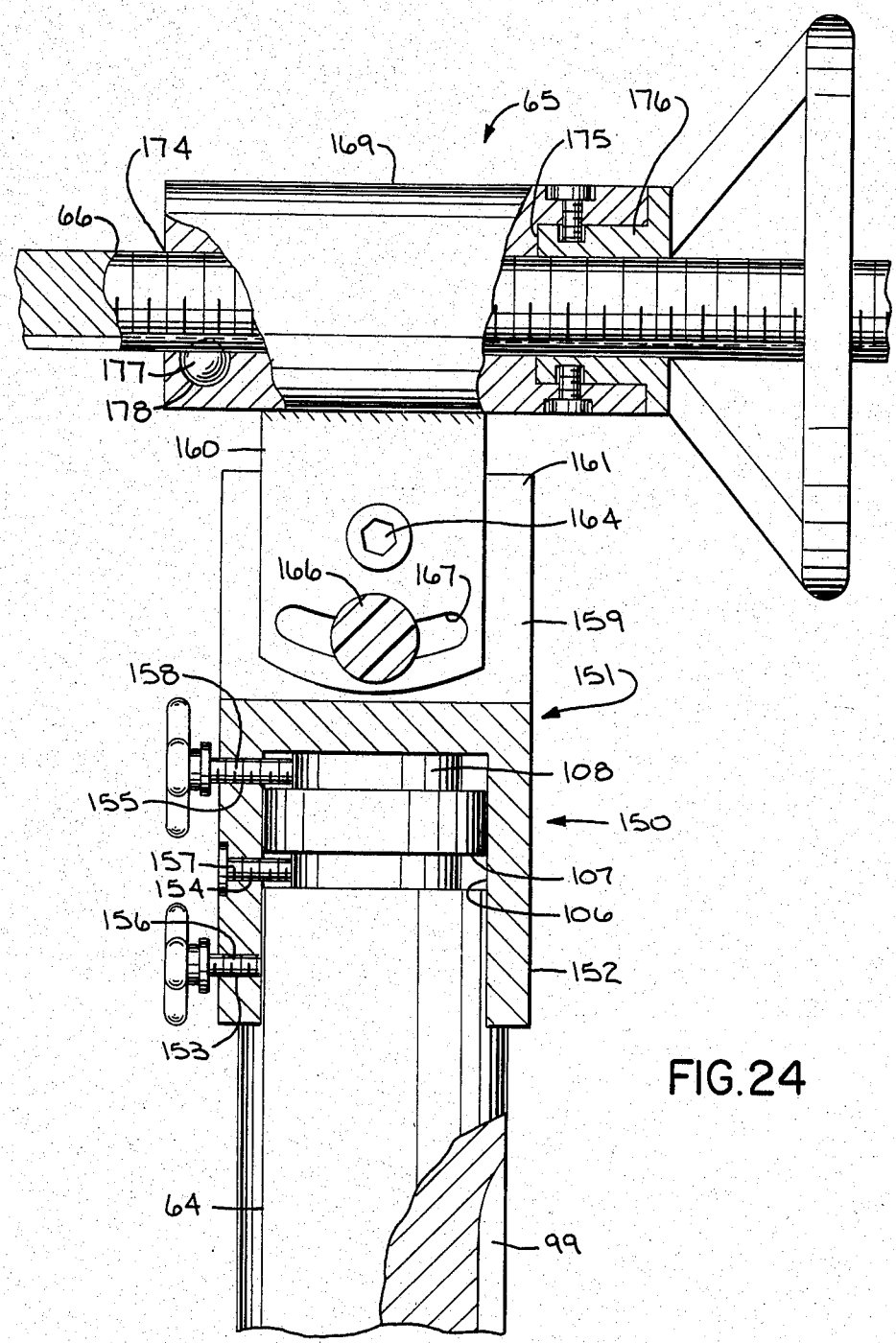
Figure 25:
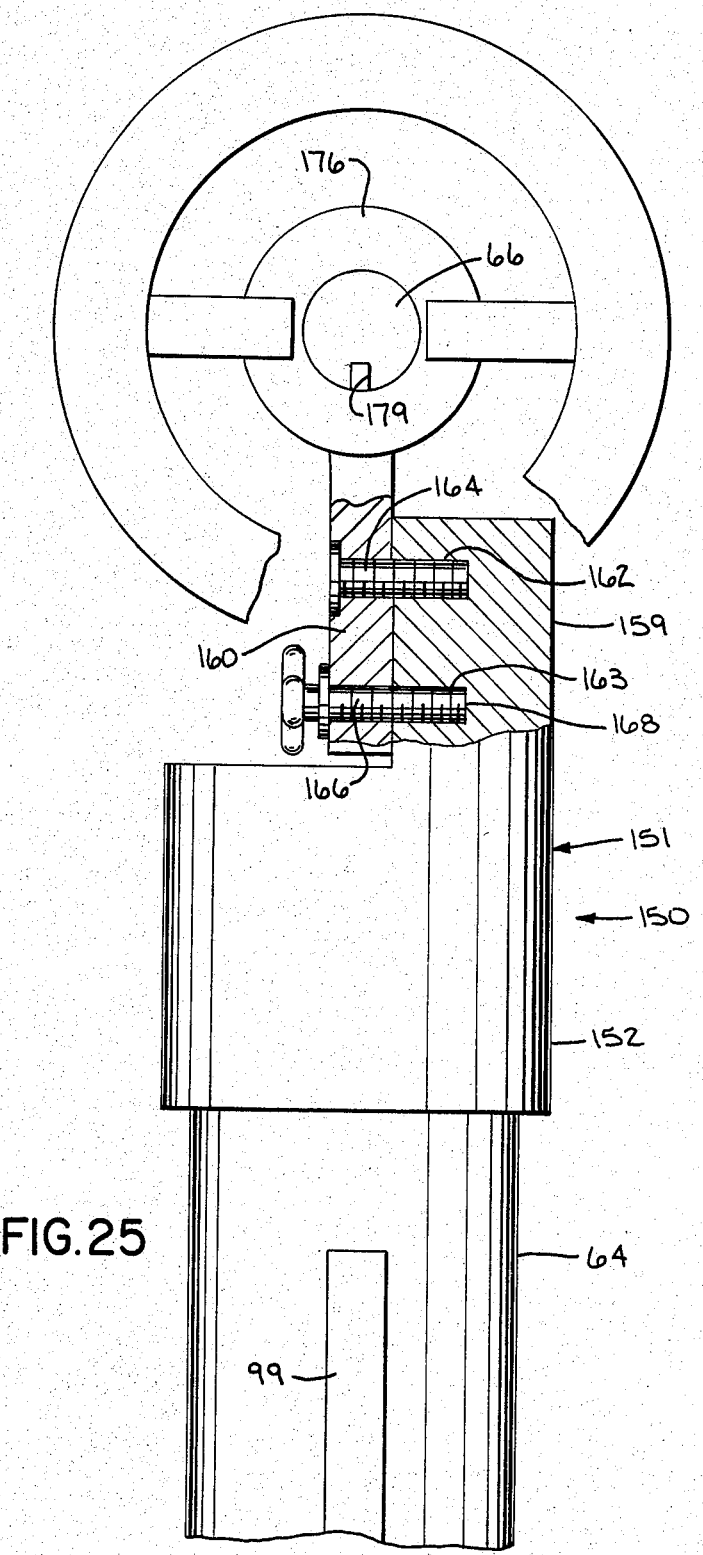
Figure 26:
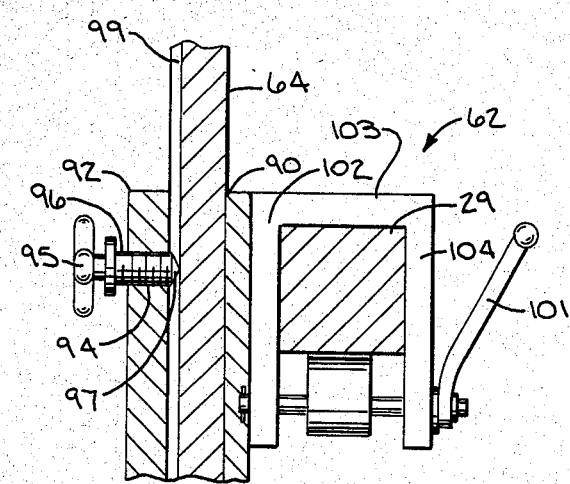
Figure 27:
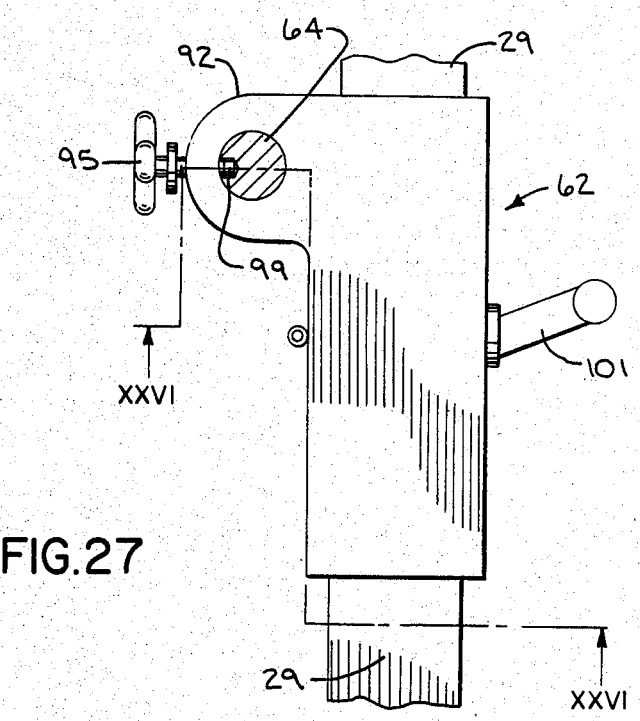
Figure 28:
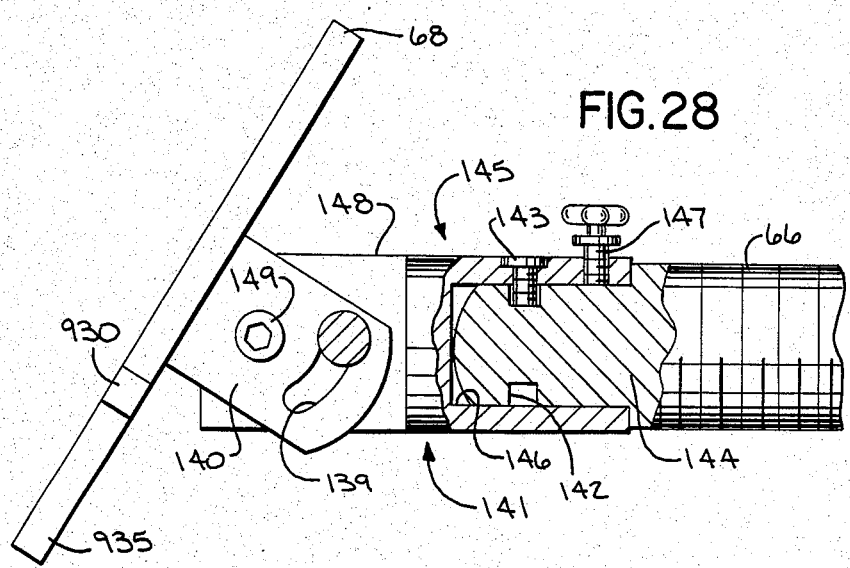
Figure 29:
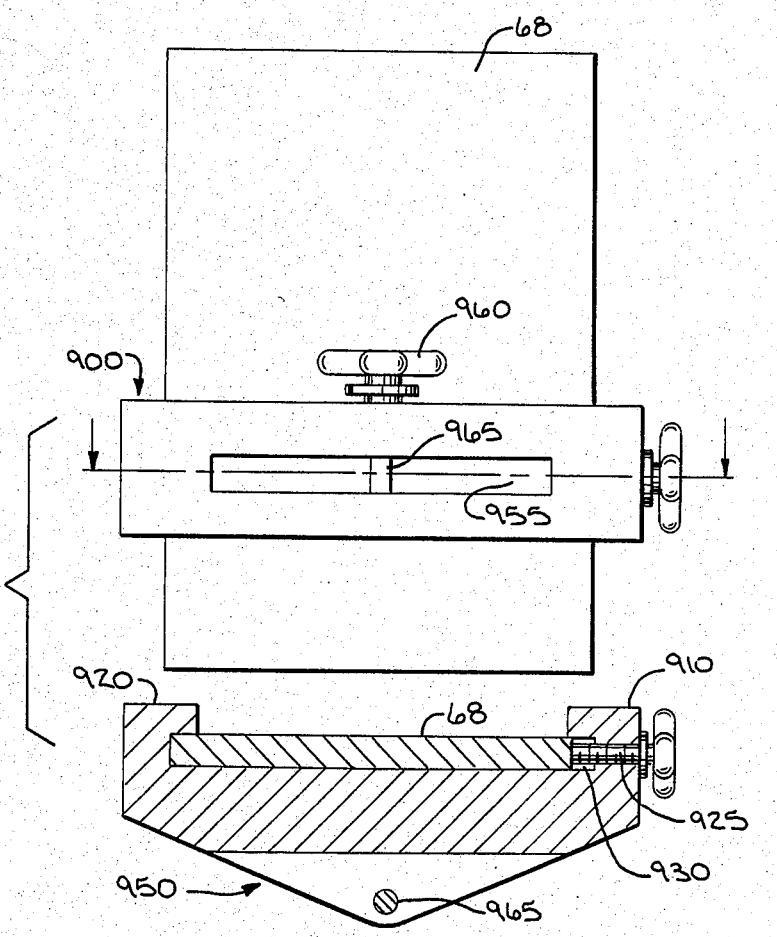

FIG. 23 a view of a vertical section through the frame of auxiliary table according to XXIII—XXIII of FIG. 1;

FIG. 24 a view of a rotary coupling and a spindle drive with portions cut away;

FIG. 25 a rearward view of the apparatus according to FIG. 24 with portions cut away;

FIG. 26 a view of a slide when being cut according to XXVI—XXVI of FIG. 27;

FIG. 27 a plan view of the apparatus according to FIG. 26;

FIG. 28 a lateral view of an extension plate swivelling apparatus, with portions broken away; and FIG. 29 a view of an attachment clamp to be utilized for extension plate under special medical conditions;

FIG. 30 a sectional view of a coupling device of a repositioning mount.

GENERAL ARRANGEMENT

The auxiliary extension table shown in perspective view in the FIGS. 1 through 3 is formed with a frame of high grade, lacquered or painted rectangular steel pipe having a double T-form in plan view and U-form in side view. In particular, a longitudinal member 12 is connected on oppositely lying ends with both a proximal transverse beam 13 and a distal transverse beam 14 as well as with a vertical free-standing support column 11 at the connection location of the proximal transverse beam 13. At each of the two lateral ends of the distal transverse beam 14, a free standing vertical post 17, 18 is fastened, so that the two posts 17 and 18 rise only about half the height of the support column 11. The support column 11 terminates above the normal working height of an operating table 5. Through this basic form of the frame, free space remains between support column 11 and each of the posts 17 and 18 as well as between the posts, that gives to the operator the greatest possible freedom of movement and also offers the possibility, in a manner hereinafter described, of coupling a repositioning mount on the longitudinal member 12 in the intermediate space between support column 11 and posts 17, 18.

At each of the lateral ends of the proximal transverse beam 13 a right foot 15 and a left foot 16, respectively, is fastened, of which the foot 15 is schematically shown in FIG. 5. Each of the two feet 15, 16 as well as each of the two posts 17 and 18 is bored out from beneath so that the casing of a commercially available roller 1, 2, 3, 4 can be inserted from beneath and anchored in the foot 15, the foot 16, and the post 17 as well as the post 18, respectively.

As FIGS. 1 through 3 further show, an arm means, indicated in its entirety with 20, serving as a carrier of an extension rod, is supported at the upper end of post 17. A similar arm means indicated in its entirety with 30 for a further extension rod is supported on the upper end of the post 18. Each of the two arm means 20, 30 is pivotable 360° about the axis of the associated post 17, 18 in a horizontal plane. On arms 29, 39 of the arm means 20, 30 there is further a lockably movable slider 62, 82 that carries a vertical guide for an extension rod 64, 84 being round in cross section and having a longitudional grove. On the upper ends of each of the extension rods 64, 84, a spindle drive 65, 85, operable through a hand wheel, is pivotally supported about a horizontal and vertical axis, so that in the illustrated exemplary embodiment the swivel range about the horizontal axis amounts to approximately 20°. By means of the spindle drives 65, 85 the spindles 66, 86 can be movable axially forwardly or rearwardly. On the ends lying opposite to the hand wheels, the spindles 66, 86 carry extension plates 68, 88 in a swivel hinge, that makes possible a lockable swinging of the extension plates 68, 88 both about the axis of the spindle 66, 86 as well as about a horizontal axis. With this concept of the adjustment possibilities, the extension plate 68, 88 can be fixed in each desired position and in each desired orientation in the space, without, as a result, impairing the referred to free working space of the operator, as well as his assistant, between support column 11 and the distal posts 17, 18, as well as the free working space between these posts through the hinging of the extension rods. The hinges and drives are maintenance and lubricant free, have high pushing or pulling load carrying capacity, and thus fulfill the particular requirements in the operating room arising out of sterile conditions.

The support column 11 supports and guides two mount-guide rods 116, 118 which are arranged parallel to the longitudinal member 12, one behind the other. The guide rods carry on the free outer ends a mounting head 190 (FIG. 18), generally denoted as mount 19 and are adjustable in height. The particularly described guiding and support of the mount-guide rods 116, 118 in the support column 11 accommodates all applied mechanical loading without elastically deforming the support column 11 or the guide rods massively formed out of high grade Niro steel. In the lateral openings of the mounting head 190, for example, a hook 199 or supporting table 250 (FIG. 20), to be described, can be inserted and locked in a defined position. The slenderness of the support column 11 with mount 19 permits the recording camera, as well as the X-ray apparatus the greatest possible freedom of movement so that the auxiliary extension table takes a minimum of space while providing complete mechanical rigidity.

Finally, it is to be particularly stressed, that the concept underlying the auxiliary extension table also permits use on the operating table 5 at an acute angle.

Central Locking

A further essential feature of the invention resides in an apparatus operable through a lever 125 in the form of a rod that simultaneously permits all of rollers 1, 2, 3, and 4 to be locked or to be freed. To that end, the casing of the two proximal rollers 1, 2, already referred to in connection with FIG. 1, is coupled with a rod 121 freely extending inside the proximal transverse beam 13. See FIG. 11.

In detail, the free ends of rod 121 extend in bore 15.5 (FIG. 5) of post 15 and in a corresponding bore in post 16, without extending into the blind central bores thereof; for post 15 the central bore 15.1 is shown in FIG. 5. The casing of the roller 1 has a through hole 15.4 of rectangular cross section which is aligned to bore 15.5 when the casing is introduced into blind hole 15.1 and fastened therein by screws inserted into bores 15.2, 15.3. A pin 15.6 of a cross section which is adapted to go through hole 15.4 is passed from outside of the post 15 through opening 15.7 (see FIG. 11) into hole 15.4 to such an extent that its inner end engages rod 121 and can be fastened to said rod 121 by screws inserted through a hole in the lower wall of proximal transverse beam 13 (see FIG. 23). Opening 15.7 is closed after assembly of the central locking device by a sealing cover. The pin cooperates with a lever mounted inside the casing such that, in a known manner, a rotation of the rod 121 and its pin clockwise causes the lever to completely lock the associated running wheel of the roller 1. Counterclockwise rotation of the rod 121 causes the lever to free the running wheel of roller 1. The opposite end of rod 121 adjacent to post 16 cooperates in the same way with a lever for roller 2 by its pin projecting laterally therefrom.

A transmission rod 120 is hinged to a downwardly extending stud 127 fastened to rod 121 adjacent to the end of longitudinal member 12 such that an axial displacement of the rod 120 results in a rotation of the rod 121 about its axis. The end of the transmission rod 120 opposite to rod 121 is hingedly connected in a similar manner to rod 122 extending lengthwise in the distal transverse beam 14. Similar to the rod 121 the opposite ends of rod 122 are fixedly connected to the corresponding lever in the interior of the casing of rollers 3,4 for blocking or freeing the associated running wheel. The connection rod 122 is also provided with a lever 125 projecting out of an opening 124 of the distal transverse beam 14 and being adapted to be manipulated by an operator's foot. The lever 125 is fastened to an L shaped member 129 threadened into a block 128 which is fixedly mounted to connection rod 122. From block 128 extends downwardly a stud 126 which carries pivotably the end of transmission rod 120. In this way through the pulling up or pressing down of the handle 125, the rod 121 as well as the rod 122, can be rotated synchronously in the locking direction or in a way obtaining loosening of the running wheels of the rollers 1 . . . 4. As the rods 120, 121, 122, run completely in the interior of the transverse beams 13, 14 as well as the longitudinal member 12 without seating, this not only withdraws them from view but also allows omitting particular bearings and supports. This housing of the central locking is thus in agreement with the easy sterility of the auxiliary table according to the invention.

The referred to casing of a wheel is located in a central bore 15.1 of foot 15 from beneath and can be secured through bolts screwed in threaded holes 15.2, 15.3. The rectangular opening 15.4 in the casing for the insertion of the right end pin 15.6 of the rod 121 is indicated in FIG. 5 by dashed line.

For the insertion of the casing for the wheels 3, 4, the lower end of post 17, as well as the lower end of post 18, is bored out as is indicated in FIG. 6 by 17.1 in connection with post 17. The holes 17.3 and 17.2 achieve the locking of the casing in the bore 17.1. The opening through which the right end of the rod 122 extends into the casing is indicated with 17.4. Apart therefrom rod 122 is connected to the rollers 3, 4 in the same way as rod 121 is connected to rollers 1,2.

As the foot 16, as well as the post 18, are formed similar to the described foot 15 as well as the described post 17, the description of this is dispensed with.

Arm Support

A further important feature of the invention is the full encasement of the arm support, the essential parts of which are apparent from FIGS. 7-10 in axial orientation. For that purpose the post 17 is fully bored out upwardly through extension of the bore 17.1 and thus represents a hollow pipe. In the upper opening of the post 17 the insert 22 is inserted and anchored through radial screws. The one piece insert 22 has an extended lower shaft 22.1, a section 22.2 extending radially outwardly fitting flush with the outer periphery of post 17 and a support shank 22.3 mounted axially above this. When the insert 22 is anchored in the post 17, the lower radially projecting shoulder 22.5 of the insert 22 rests on the upper face 17.6 of the post 17.

To the arm support 20 further belongs a lower locking disc 24, whose central passage 24.1 surrounds the support shank 22.3 with clearance, when the lower locking disc 24 is threaded on the upper annular shoulder 22.6 of the section 22.2 in the axial direction. On the upper side, the radially widened bore 24.1 is surrounded by a tooth rim 24.6 with upwardly projecting, radially extending teeth 24.2.

A further part of the arm support 20 is the upper locking disc 26 which has a central support casing 26.2 extending in an axial direction. The inside dimension of the support casing 26.2 is slightly larger than the outer diameter of support shank 22.3 so that the support casing 26.2 after the attachment on the support shank 22.3 rotatably surrounds this without radial play. The outer diameter of the lower part of the support casing 26.2 is smaller than the inside dimension of the bore 24.1. The support casing 26.2 is surrounded by a radially extending ring 26.3, the downwardly directed face of which is provided with a rim of locking teeth 26.4. The radially extending teeth 26.4 are formed to coact with the teeth 24.2 of the lower locking disc 24, when the upper locking disc 26 so surrounds the support shank 22.3 that the lower portion of the support casing 26.2 is rotatably arranged between support shank 22.3 and the inner wall of the bore 24.1 of the lower locking disc 24 threaded on the insert 22.

To the arm support further belongs an arm head 28, which is provided as a downwardly opening container like element with a lateral recess 28.4, the side walls 28.6, 28.7, 28.8 (and the not shown front side wall) of which define a square for inserting and fastening horizontally the arm 29 of squared transverse cross section therein. The inside dimension of the internal bore 28.1 of the container element is only slightly larger than the greatest outer diameter of the upper locking disc 26, as well as the greatest outer diameter of the lower locking disc 24 and as well as the outer diameter of the section 22.2 on the insert 22. The arm head 28 has, further, in its base 28.2 central bore 28.3.

When the upper locking disc 26 is threaded into the base 28.2 of the arm head 28 aligned to bore 28.3 in axial direction the arm head 28 with the upper locking disc 26 is placed on the support shank 22.3, the outer wall 28.5 of the arm head 28 surrounds both the locking discs and a major portion of the section 22.2. When the locking teeth 26.3 and 24.2 are in engagement, the part of the upper locking disc 26 extending radially outwardly from the support casing 26.2 forms a ring-like chamber 26.8 with an upper radially extended portion of bore 24.1, in which not disclosed coil spring packets are inserted. In the released condition, these hold the locking teeth 26.4 and 24.2 out of engagement.

The arm support 20 is held together through a cam 27 (FIG. 1) provided with a hand lever, on which a threaded shank is coupled that is threaded through the bore 28.3 into the inner thread of a blind hole 22.7 in the support shank 22. When the lever of the cam 27 shown in FIG. 1 is turned downward into the hole 22.7, the cam presses on the upper surface of arm head 28 such that the upper locking disc 26 so compresses the coil spring packet in the chamber 26.3, and the locking teeth 26.4 and 24.2 come into engagement. In this way, the arm can be definitively arrested by means of the operation of cam 27 at angular locations fixed through the spacing of the locking teeth 26.4 and 24.2, and may be swung in a horizontal plane when cam 27 is loosened.

This incremental adjustability of the arm 20 within the horizontal plane however causes no problems in the practical use of the auxiliary table, because, for example, if required, the carriage 62 is drawn from the arm 29 and again placed on the arm 29 in a 180° reversed direction. Thus as well, through the remaining link of the extension rod connected with arm 29, a continuous adjustment of the extension plate 68 is in each case achieved, as will be appreciated from the following description of the extension device.

The arm support operates maintenance free and insures against soiling through the cup formed configuration of the arm head 28, and can be very easily externally cleaned. It is to be understood that arm support 30 is constructed identical to arm support 20.

Extension Device

The auxiliary table includes two distal extension devices each of which is mounted to the horizontal arm 29 and the horizontal arm 39, respectively. As both extension devices are of identical construction, only the extension device mounted to arm 29 is described hereinafter in detail.

The extension device removably coupled to horizontal arm 29 includes the extension rod 64, the spindle 66 which is fastened to the extension rod 64 by the spindle drive 65, and a swivel arm 160 and a rotary coupling 150 (see FIG. 24), and the extension plate 68 coupled to the free end of the spindle 66 by a swivel member 140 and a rotary coupling 130 (see FIG. 28). The extension rod 64 is removably received in a bore 90 through a lug 92 of the slider 62 (see FIG. 26). Through a threaded hole 94 in the wall of the lug 92 extends a clamping screw 96 having a handle 95 on the outer end. The tip 97 of the screw opposite to the handle projects into a longitudinal groove 99 of the extension rod 64 and clamps the extension rod 64 within the bore 90 when the screw 96 is turned into the hole 94 to a sufficient extent. The depth of the groove 99 increases slightly from the end of the extension rod 64 near the spindle 66 to the opposite free end thereof. Thereby, when the screw 96 is only slightly turned outwardly from its clamping position the extension rod 64 is prevented from escaping rapidly into its lowermost position with respect to arm 29.

According to FIGS. 26 and 27 the slider 62 has a channel formed by three side walls 102, 103, 104, side walls 102 and 104 rectangularly joining side wall 103, and altogether defining an aperture of the channel the width of which is adapted to the squared cross section of arm 29 so as to receive and to ride on arm 29. By turning a clamping lever 101 the slider 62 can be maintained fixedly in a selected position on arm 29 by clamping means 105.

The lug 92 is formed from the outer surface of side wall 102. Therefore, an operator may remove the slider 62 from the horizontal arm 29 and turn it for an angle of 180° about a vertical axis and push the slider 62 again onto the arm 29. Thereby the vertical position of the extension rod 64 is offset laterally with respect to the arm 29 and extends along the other side thereof. Alternatively, after having withdrawn the slider 62 from arm 29 it may be turned by 90° about a horizontal axis and may be again clamped upon the arm. The extension rod 64 then extends horizontally either below or above the arm 29 depending upon whether the slider 62 has been turned clockwise or counterclockwise by 90° about said horizontal axis. Such manipulations are possible because of the squared cross section of arm 29 and the correspondingly squared aperture of the channel of the slider 62.

FIGS. 24 and 25 show the structural features of the spindle drive 65 and the swivel arm 160 and the rotary coupling 150. The upper end of the extension rod 64 having a ring groove 107 and an end portion 108 of polygonal periphery is received in a recess 106 of a coupling head 151. Three threaded holes 153, 154, 155 are provided in a ring skirt 152 defining the recess 106. A locking screw 156 is threaded into the lowermost hole 153, a different locking screw 158 extends into the uppermost hole 155 and a set screw 157 is fixedly journalled into hole 154. The inwardly projecting end of set screw 157 fits into the ring groove 107 so that coupling head 151 may be rotated coaxially to the extension rod 64 when locking screws 156 and 158 are loosened. Tightening locking screw 156 and loosening screw 158 allows clamping the coupling head 151 in any desired angular position with respect to extension rod 64. On the other hand, tightening locking screw 158 against any of the polygon peripheral surfaces of end portion 108 while locking screw 156 is disengaged from extension rod 64 allows for clamping the coupling head 151 in any distinct angular position as defined by the polygon peripheral surfaces of the end portion 108.

The top 159 of the coupling head 151 opposite to the skirt 152 has reduced radial extension and is provided with a plane surface 161 extending parallel to the axes of extension rod 64. Two transverse threaded holes 162 and 163 one above the other are bored into the top 159. A pivot pin 164 is inserted into a mating hole 165 of the swivel arm 160 and is anchored within the uppermost hole 162 of the coupling head top 159 so that swivel arm 160 may pivot about pin 164. A clamping screw 166 having an outwardly projecting handle is received within a curved slot 167 in the lower portion of swivel arm 160. The threaded end section 168 of the clamping screw 166 opposite to the handle thereof is journalled into the lowermost hole 163 of top 159. Thus, swivel arm 160 together with the rest of the extension device connected to the swivel arm 160 may be swung about pin 164 parallel to surface 161 to an extent as defined by the curved length of slot 167.

Swivel arm 160 is welded to the periphery of a sleeve 169 of spindle drive 65. The sleeve 169 has an axial through bore 174 for receiving the spindle 66 which at one end of the sleeve 169 is widened by a radial outwardly extending shoulder 175. A nut 176 is rotatably mounted within a widened section of bore 174 and abuts shoulder 175. Outside the sleeve 169 the nut 176 is coupled to a hand wheel for manually turning nut 176 which engages the thread of spindle 66 by its mating inner thread. Adjacent the end of the sleeve 169 opposite to the widened section of its bore 174 a ball bearing 177 is mounted such that the outer ring cage 178 thereof may freely rotate about an axes transverse to the spindle 66. The ring cage 178 runs in a longitudinal groove 179 of the spindle 66 for preventing rotation of spindle 66. Thus, the spindle 66 may be shifted lengthwise by rotating nut 176.

Spindle 66 terminates in an end portion 144 configured similarly to the end portion of extension rod 64 which is received in the recess 106. End portion 144 is received in a recess 146 of a head 141 of a rotary coupling 145 and has a ring groove 142 for rotatably mounting the cupping head 141 on the end portion 144 by a set screw 143. The rotary coupling 145 may be clamped in any angular position about the axis of the spindle 66 by a clamping screw 147. The head 141 has a top 148 similarly configured as top 149. A swivel arm 140 similar to a swivel arm 160 is welded reawardly to the rectangular extension plate 68. Thus, extension plate 68 may pivot about pin 149 extending transversely to the axes of spindle 66 to an extent as defined by the curved slot 139.

The extension device described above has in summary such a great number of adjustment possibilities that the extension plate 68 may be adjusted in virtually any desired position in space. The device may be rotated firstly about the vertical axis of post 17 by loosening clamp 27, and secondly about the vertical axis of extension rod 64 by loosening clamping screws 156, 158. Moreover, extension plate 68 may be displaced forwardly or reawardly by turning nut 176 manually by the handle coupled thereto. Additionally, the extension plate 68 may be lowered or raised by loosing clamping screws 166 and the clamping screw extending through slot 139. Last not least, the extension plate 68 may be swung about the axis of the spindle 66 by loosing clamping screw 147. Additional possibilities of adjustment are offered by attaching slider 62 in a desired orientation on arm 29 as explained above. Remarkably, all these adjustments can be effected without moving the auxiliary table 50 on the floor, i.e. by maintaining simultaneously an adjusted position of the mount and the associated support plate to be described hereinafter.

Mount

A further important feature of the invention is the distortion free journalling of the guide rods 116, 118 as well as the configuration of the mount 19.

For this, a support bush 110 formed of brass is anchored in the upper end of support column 11 and, as shown in FIGS. 12 and 13, is penetrated by two parallel longitudinal bores 112, 114. The length of the guide bush 110 is determined approximately in accordance with the moment exerted and absorbed from hook 199 in mount 19 and is many times greater than its width. The longitudinal bores 112, 114 are so finely finished that the guide rods 116, 118 for the mount 19 are guided in the longitudinal bores 112, 114, without radial play and also are easily axially movable. One of the two guide rods 116, 118 formed of high strength Niro steel has on its lower end a not disclosed radially projecting boss limiting the maximum height extension by cooperation with the lower end surface 111 of the support bush 110. The other of the pair of guide rods 116, 118 has a radial elongation limiting the maximum sliding in of the guide rods, that cooperates with a not shown abutment in the inside of the support column 11, the abutment being so arranged on the support column 11, that with the descent of the guide rods 116, 118, fingers cannot be pinched between a mount head plate 192 of the guide rods and the upper end of the guide column 11.

The support bush 110 has a radial recess 117 in which a wedge body 119 can be wedged against guide rods 116, 118 in the manner shown in FIG. 14 by means of a knurled screw 115 operable from the outside for the height locking of the guide rods 116, 118.

The guide column 11 is sealed with the inserted support bush 110 through a plate 130 (FIG. 15), that has bores 131, 132 for the guide rods as well as ring nuts 133, 134 respectively surrounding these bores. In each of the two ring nuts 133, 134 a ring gasket is inserted with a ring formed wiper lying against the respective guide rod 116, 118. Thus the intrusion of dirt in the support bush 110 is reliably prevented. As can be appreciated from FIG. 13, 14, and 15, the guide rods 116, 118 are supported in a direction one behind the other in the support bush 110 with reference to the longitudinal direction parallel to the longitudinal member 12. Alternatively, the guide rods 116, 118 can also be supported transversely next to each other, if the thereby produced greater width of the support column 11 can be tolerated.

The guide rods 116, 118 are connected on their upper ends with a head plate 192 (FIGS. 16,17) and anchored in the blind holes 197, 198 of the head plate 192 by means of steel pins driven in two sets of holes 193, 194, and 195, 196 of the head plate 192. As is particularly shown in FIG. 17, the head plate 192 possesses in each of its four corner regions a hole 172, 173, 174, 175, through which bolts that can extend upwardly for the fastening of the mounting head 190. Further, a plurality of pin holes 176, 177, 178, 179 are provided, in which can be inserted locking pins, the free ends of which extend in the mounting head 190 for the additional adjustment and stabilization.

The mounting head 190 has the form of a table with table plate 189 and four corner legs 181, 182, 183, 184. The mounting head 190 stands with these legs on the upper face 191 of the head plate 192 and is bolted and pinned to this in the referred to manner. The head 190 together with its legs 181, 182, 183, 184 is milled out of a massive block. Between the corner legs 181, 183 as well as 182, 184, an intermediate space of defined width, which when the head 190 is fastened to head plate 192 forms together with the upper face 191 of the head plate 192 an insertion channel 186 for inserting an arm, e.g. of the mount-hook 199. A not shown pin that extends from a bore 170 in the lower surface of the table plate 185 between the legs 182, 184 into aligned hole 172' of head plate 192 serves for the establishment of a defined insertion of the hook 199.

A further, transverse lying insertion channel 187 is laterally bordered by the legs 181, 182, as well as 183, 184 so that the hook 199 can be inserted in mounting head 190 in three different directions lying at right angles to each other and can be fastened there by means of a knurled screw extending through a middle hole 188. It will be understood that the hook 199 terminates in a rectangular bar, the overall dimensions of which are proportioned to the insertion channel 186 and the transverse lying insertion channel 187.

Support Plate

A further important feature of the invention is embodied in the support plate 250 shown in FIGS. 20 and 21 attachable on the mounting head 190. The support plate 250 is formed out of pure polypropylene and is fully transparent to X-rays. It has a width sufficient to the support of the buttock of the patient and is rounded to a point on its narrow side 251. In this hand region the support plate has a hole 252. On the underside, plate part 254 is provided beneath the region 251, which possesses an outer contour similar to the border of the region 251 and on the inner edge merges into a web 256 extending upwardly to the plate 250. The web 256, as shown in FIG. 21, surrounds the hole 252 inwardly in some distance and is bent in the opposite sense to the tip contour of the region 251 and acts as a reinforcement for the region of the hole 252. Altogether, there thus results a cradle formed out of the part 251, the web 256 and the plate part 254 that is rearwardly stiffened through a further rearward bar 258 connecting the rearward portion of plate 254 to the lower surface of plate 250. The thus named parts are integrally formed in the support plate 250 and are similarly formed out of pure polypropylene. A bore 253 provided with interior threads is cut in the plate part 254 in alignment with the bore 252.

A mounting post 240 possesses in its lower part shown in FIG. 20 an upwardly running conical enlargment 242 that runs radially inward at 248 to a pin 244. The pin 244 is provided, at least on the lower end, with outer threads so that the mounting post 240 can be screwed in the threaded hole 253 until the annular shoulder 248 rests on the upper surface of the support plate around hole 252 (FIG. 20). In the region of the conical enlargement 242 and on the inside of the pin 244 a steel bar 246 is typically embedded in the mounting post 240 formed out of pure polypropylene.

The internal dimension of the cradle is so sized that it can contain the end of a rectangular steel bar 260 the remote end of which, not disclosed in FIG. 20, can be introduced into one of the channels 186, 187 of the mounting head 190. The bar 260 possesses a hole 262, through which the pin 244 extends. One can see that the support plate 250 can be pivoted laterally about the pin 244 in the bore 262 of the bar 260 about the axis of the mounting post 240. The mounting post 240 and the support plate 250 are transparent to X-rays so that the provision of the X-ray picture in the thigh-neck region is not hindered. Further, the support plate 250 can be swung out of the way to the side if a cast is to be put on the patient.

Repositioning Mount—Coupling Device

A further important feature of the invention is found in the coupling device of the repositioning mount, that makes possible an expansion of the auxiliary table described so far to a repositioning-extension-auxiliary table. As FIGS. 3 and 4 particularly show, the repositioning mount according to the invention is formed of a carriage that in the plan view forms a welded H-frame with transverse members 52 and 56 and a mount-longitudinal member 54 connected intermediate the former members. To each of the laterally outward ends of the members 52 and 56 a conventional roller is mounted so that the reposition mount 50 may be run freely on the floor. In the middle of the transverse member 52 a stanchion, indicated in its entirety with 520, is fastened in free standing fashion, and a similar stanchion 540 is centrally fastened on the transverse member 56. The stanchions 520 and 540 are connected, on their upper ends, with a table 510 extending parallel to the mount-longitudinal member 54, on which two supports 600 and 800 are transversely and are lockably displaceable. Each of the supports 600, 800 carries a fixing ring 650 and 850. Each of the two fixing rings 650 and 850 is fastened on the associated support 600, 800 so as to be laterally and vertically adjustable in the manner evident from FIG. 4.

An essential feature of the repositioning mount indicated in its entirety by 50 lies in the height-adjustability of the table 510 by means of a hand wheel 530 that is provided on one end face of the table 510 and in to be described manner synchronously adjusts two spindle drives respectively arranged in the stanchions 520 and 540.

The rigid coupling of the repositioning mount 50 on the auxiliary table is successfully obtained through two measures; the height of the frame of the repositioning mount 50 formed by members 52, 54 and 56 is smaller than the spacing of the lower edge of the longitudinal member 12 from the running plane of the running wheels of rollers 1, 2, 3, 4. Thus the frame of the repositioning mount 50 can be moved under transverse member 12 into the space between column 11 and posts 17, 18 up to engagement of longitudinal member 12 to abutment studs 55, 57 fastened to and rising above mount-longitudinal member 54. From FIG. 3 it can be seen that the overall length of the reposition mount is smaller than the distance between column 11 and posts 17, 18 which allows easy attachment of the reposition mount to the auxiliary table between column 11 and posts 17, 18.

The second measure is the coupling device 580 on the mount-longitudinal member 54 shown in detail in FIG. 30. The coupling device includes a hollow rectangular cross member 585 welded on mount-longitudinal member 54 between studs 55 and 57, and a shaft 590 supported by and extending through the cross member 585 transversely to mount-longitudinal member 54. The cross member 585 has opposite side walls 583, 584 through which aligned bearing holes 586, 587 for rotatably supporting the shaft 590 are bored. A spring box 589 surrounding bore 587 of side wall 584 is drilled out from side wall 584 for housing a coil spring or spring package 591 through which shaft 590 extends axially. An abutment disc 592 is secured on shaft 592 which closes spring box 589 outwardly. An additional abutment disc 593 is fixedly fastened to shaft 590 outside hole 586 of side wall 583. Thus, the spring 591 urges resiliently the shaft 590 in direction of an operating lever 595 mounted to the end 596 of shaft 590 which projects out of side wall 584. However, as disc 592 has a diameter not greater than the diameter of spring box 589 the shaft 590 is supported also in cross member 585 so as to move axially against the force exerted by spring 591 if an axial pull acts on shaft 590.

Locking device 58 is secured to the end of shaft 590 opposite to the end 596 and projecting out of bore 586, and consists substantially of a plastic wedge body 597. The axial thickness of wedge body 597 increases radially so that wedge body 597 has a semiconical cross section as seen in the view of FIG. 30. Wedge body 597 is unrotatably mounted to shaft 590 such that a locking wedge surface 599 extends with an angle different from 90° to the axes of shaft 590 while the opposite surface thereof extends transversely to shaft 590 and is backed up by a cover plate 598 also fastened to shaft 590 which prevents axial bending of body 597. The peripheral surface of the wedge body 597 has a flattened portion 579 such that the wedge body 597 and the cover plate 598 do not project above the upper surface of rectangular cross member 585 when the shaft is turned into an inoperative position as shown in FIG. 30 in full lines.

For locking the reposition mount 50 to the auxiliary table operating lever 595 is thrown to a position wherein the flattened portion 579 of the wedge body peripheral surface faces upwardly and consequently does not project above mount-longitudinal member 54. Reposition mount 50 is then slid towards longitudinal member 12 until longitudinal member 12 abuts studs 55 and 57. Operating lever 595 is now thrown into operative position whereby wedge body 597 engages longitudinal member 12 by its wedge surface 599 and presses it resiliently (by spring 591) against studs 55 and 57 which may be covered by plastic material. A safe and firm coupling of reposition mount 50 to the auxiliary table is thereby effected so that both can be run as a unit across the floor and arrested in a desired position by manipulating the lever 125 of the central locking described above.

It is thus possible in cases in which a repositioning of a fracture is not necessary to free the auxiliary table from the then not required repositioning device. But if required, the auxiliary table can be furnished with the rigidly couplable repositioning device 50.

Height Adjustment of the Repositioning Table

In each stanchion 520, 540, a device is housed that is schematically illustrated in FIG. 22 and is described in connection with the stanchion 520. On the transverse member 52 a rigid pipe element 532 is anchored, in the upper opening of which a nut 526 having an inner thread 527 is inserted and fastened. A stanchion head 534, bolted to the lower surface of the table 510, has in the lower part a wide axial bore 533, in which a shielding pipe 522 is mounted. The interior width of the covering pipe 522 is slightly larger than the largest outer diameter of pipe element 532, respectively nut 526. A central hole 539 in the bottom 543 of bore 533 accommodates the shaft 545 of a spindle which is rotatably held by a ball bearing 544 press fitted on an axial extending shaft 545 of spindle 524 and housed in a cup-like recess 546 drilled out from the side of head 534 opposite to bore 533. The upper end of shaft 545 carries unrotatably a bevel gear 547 which meshes with a second bevel gear 548 unrotatably fixed to a shaft 550. Shaft 550 extends transversely to spindle 524 through aligned holes of a top collar 536 of the head 534.

Shaft 550 extends also through aligned openings in a similar stanchion head 514 of stanchion 540 and runs parallel to the top plate 552 of repositioning table 510. On the end of this shaft extending outwardly to the side of the table 510, the adjustment wheel 530 can be mounted. The repositioning table 510 has depending side walls 511, 512 which are fastened on either side of top collar 536 on a stepped-in shoulder 542 provided in the periphery of head 534. The table 510 and the head 534 rest on a pressure bearing 523 which is supported by a radially outwardly extending ring shoulder 525 of the spindle 524 and fitted into bore 533 and the upper end of shielding pipe 522. The outer thread of the spindle matingly engages the inner thread of nut 526.

On the lower end of the shielding pipe 522, a bushing formed out of three half shells is inserted in a recess in the inner surface of the shielding pipe. This makes possible an exact guiding of the shielding pipe 522 on the outer periphery of the pipe element 532.

When the adjustment wheel 530 is rotated, the shaft extending through the opening 535 and the bevel gear 548 rotate, which through the bevel gear 547 rotates the spindle 524, which, however, cannot be displaced axially. The spindle rotating on the stationary nut 526 raises or lowers itself and the head 534 and the table 510 coupled to it, correspondingly. As a similar drive apparatus is housed in the stanchion 540, through the rotation of the handwheel 530, the spindle drives mounted in both stanchions 520 and 540 are synchronously moved so that the table 510 rises or lowers while simultaneously maintaining its upper surface horizontally.

The spindle drive is not only maintenance free but also through the long, depending pipes 522 and 542, is fully insured against soiling by sealing rings not shown sealing the lower ends thereof to the periphery of pipe elements 532 and 562. The stanchions 520, 540 of the repositioning mount thus permit extraordinarily easy and complete cleaning. The invention provides also a particular form of the extension plate 68 for easing attachment of a number of auxiliary devices depending the particular medical situation. An example of such auxiliary device is a locking device shown in FIG. 29. The locking device consists of a clamp 900 bracketing laterally the extension plate 68 by brackets 910, 920. One of the brackets 910 is equipped with a clamping screw 925, the tip of which extends into a notch 930 in the side face 935 of the extension plate 68. The locking device has an angulared front section 950 which is slit transversely. The slit 955 is traversed by pin end 965 of a screw 960 journaled into a threaded hole from above the section 950. The locking device is omitted from FIG. 28 for the sake of clarity. In use a not shown horse shoe like member spanning a wire which is shot through the foot of a patient, may be held by the locking device. To this end the member having adjustment holes is placed partially into the slit such that the pin end 965 may extend through a desired one of said adjustment holes.

While a particular exemplary embodiment of the invention has been disclosed, it will be immediately obvious to one skilled in the art, that the invention in its details is not limited to the disclosed device.

I claim:

1. An auxiliary table for the medical treatment of an extremity in preparation for pinning of bones or the like, said table providing ready access to the treatment site by equipment and personnel and comprising:
    a frame movable on rollers, said frame being formed by a horizontal longitudinal member (12) having a proximal end and a distal end, said member being fastened to the centers of horizontal transverse beams (13, 14) at each of said proximal and distal ends of said member;
    a vertical support column fastened on the proximal end of said member and carrying a vertically adjustable mount (19);
    two free-standing vertical posts, said posts being mounted at horizontally spaced apart locations on either side of the center of said distal end beam, each of said vertical posts carrying a vertically and pivotally adjustable extension device (20, 30), the horizontal spacing of said posts providing access to the treatment site from the distal end of said table said member, mount and posts presenting an upstanding U configuration to the auxiliary table in side elevation, said U configuration being unobstructively open at the top to provide access to the treatment site from the sides of said table.

2. The auxiliary table according to claim 1 wherein said two spaced apart, free standing vertical posts are mounted on the ends of said transverse beam mounted on said distal end.

3. The auxiliary table according to claim 1 characterized in that the longitudinal member (12) and the transverse beams (13, 14) are of hollow profile and in which extend linkage bars (120, 121, 122) of a central locking means for the rollers (1, 2, 3, 4) operable from the outside (with 125).

4. The auxiliary table according to claim 3 characterized in that each roller (1 ... 4) has a casing held in one of feet (15, 16) of the transverse beam mounted on said proximal end and in posts (17, 18), and a member is movably mounted in said casing for the locking of the running wheels of said rollers and in that the rods (120, 121, 122) for the central locking means are journalled in the casing of the rollers.

5. The auxiliary table according to claim 3, characterized in that the transverse beam (14) mounted on said distal end possesses a rear opening (124) out of which extends an operating lever (125) connected with the rods (120, 121, 122) for the central locking means.

6. The auxiliary table according to claim 1 characterized in that the lower edges of the longitudinal member (12) have a spacing from the running plane of the running wheels of said rollers, such that the longitudinal member and the transverse beams of the carriage (52, 54, 56) of a repositioning table (50) can be moved beneath them.

7. The auxiliary table according to claim 1, characterized in that each extension device (20, 30) includes an extension plate (68, 88), which may be rotated for 360° about the axis of an extension rod (64, 84) removably coupled to the vertical post (17, 18).

8. The auxiliary table according to claim 1 characterized in that each extension device (20, 30) includes an extension plate (68, 88) coupled to an extension rod (64, 84) by a spindle (66, 86), which may be swung about an axis transverse to the spindle and the extension rod.

9. The auxiliary table according to claim 1 characterized in that each extension device (20, 30) includes an extension plate (68, 88) coupled to an extension rod (64, 84) such that the extension plate may be swung about the axis of the extension rod (64, 84).

10. The auxiliary table according to claim 9 characterized in that the extension plate may be clamped to the extension rod at distinct angular positions.

11. The auxiliary table according to claim 9 characterized in that the extension plate may be clamped to the extension rod at any desired angular position.

12. The auxiliary table according to claim 7 characterized in that the extension plate is coupled to a horizontally rotatable arm (29, 39) by a slider (62, 82) which may be withdrawn from and attached to the arm in angular positions deviating from each other by 90° or a multiple thereof.

13. An auxiliary table according to claim 1 characterized in that a support bush (110) is anchored in the support column (11), the length of said bush being essentially larger than its width, said bush having two parallel passages (112, 114) extending therethrough for the mount guide rods (116, 118).

14. The auxiliary table according to claim 13 characterized in that the support bush (110) has a lateral opening (117) for a wedge body (119) for the height locking of the mount-guide rods (116, 118).

15. The auxiliary table according to claim 13 characterized in that on the mount-guide rods (16, 18) is mounted a mounting head (190, 192) that has at least one lateral opening (186, 187) for the lockable insertion of at least one of a mounting-hook (199) or support plate (250, FIGS. 20 and 21).

16. The auxiliary table according to claim 15 characterized in that the mounting head has two lateral insertion channels (186, 187) rectangular in cross section laterally displaced at 90°.

17. The auxiliary table according to claim 15 characterized in that a support plate (250) transparent to X-rays is inserted in the opening (186, 187) of the mounting head.

18. The auxiliary table according to claim 17 characterized in that the support plate (250) is pivotally supported about a vertical axis on an arm (260) insertable in the opening (186, 187).

19. The auxiliary table according to claim 17 characterized in that the support plate is formed out of polypropylene.

20. The auxiliary table according to claim 17 characterized in that the support plate (250) is rotatably supported about a shaft (244) on an arm (260), that is provided, at least in the pivot area, with a steel core and is otherwise formed out of X-ray transparent plastic.

21. The auxiliary table according to claim 1 characterized in that each of the extension devices (20, 30) is formed out of an arm (29, 39) with a squared profile and an arm head (28, 38) that is supported pivotally about a vertical axis for 360° rotation the posts (17, 18).

22. The auxiliary table according to claim 21 characterized in that the arm head (28, 38) has a downwardly extending casing (28.5) about the upper end of the post (17, 18) enclosing a support for said arm.

23. The auxiliary table according to claim 22 characterized in that inside the casing (28.5), two locking discs (24, 26) are arranged in vertical alignment one above the other and engage by means of radial locking teeth (24.2, 26.4).

24. The auxiliary table according to claim 23 characterized in that the upper locking disc (26) secured with the arm head (28, 38) has an axial support bush (26.2), which embraces an upright standing shaft (22.3) of an insert (22) inserted in the upper end of the posts (17, 18) without radial play.

25. The auxiliary table according to claim 24 characterized in that between the upper locking disc (26) and the lower locking disc (24) connected with the insert (22), an annular chamber (24.3) is formed radially within the locking tooth hub (24.2, 26.4), in which a plurality of flat coil springs actuatable in the axial direction are housed.

26. The auxiliary table according to claim 25 characterized in that an upwardly open, threaded blind hole (22.7) is formed in the support shaft (22.3) of the insert (22) in which the threaded shank of a cam lever (27, 37) extending axially upwardly out of the arm-head (28, 38) is anchored, which acts on the arm-head (28, 38) against the action of the flat coil springs.

27. The auxiliary table according to claim 21 characterized in that each arm (29, 39) has a movable clamping slider (62, 82), which has a vertical guide for an adjustable height extension rod (64, 84).

28. The auxiliary table according to claim 27 characterized in that the extension rod (64, 84) has a longitudinal groove (99) for preventing rotation of the extension rod within the guide.

29. The auxiliary table according to claim 28 characterized in that the depth of the groove (99) increases continuously towards the free end of the extension rod.

30. The auxiliary table according to claim 27 characterized in that on the upper end of the extension rod, a spindle (66, 86) is axially displaceable as an extension bar and is pivotally supported about a horizontal axis.

31. The auxiliary table according to claim 30 characterized in that the proximal end of the spindle (66, 86) carries an extension plate (68,88) that is pivotally supported on the spindle end about two axes transverse to one another.

32. The auxiliary table according to claim 1, characterized in that between support column (11) and posts (17, 18) is detachably fastened a repositioning mount (50) on the longitudinal member (12).

33. The auxiliary table according to claim 32 characterized in that the carriage (52, 53, 56) of the repositioning mount (50) is formed of a mount-longitudinal member (54) and two transverse members (52, 56) and said carriage has a smaller height than the lower edge of the longitudinal member (12) of said table.

34. The auxiliary table according to claim 33 characterized in that in the mount-longitudinal member (54) a shaft (590) parallel to the transverse members (54, 56) is axially resiliently mounted, said shaft carrying on one end an operating lever (53) and on the oppositely lying end a wedge body element (597).

35. The auxiliary table according to claim 34 characterized in that the wedge body element (597) is a reinforced plastic disc, the axial thickness of which increases in the circumferential direction for coupling the longitudinal member (12) of said table to the carriage.

36. The auxiliary table according to claim 33 characterized in that the mount-longitudinal member (54) carries at least one upwardly projecting stud (55, 57) as an abutment means for the longitudinal member (12) of said table.

37. The auxiliary table according to claim 36 characterized in that the studs are covered with plastic.

38. The auxiliary table according to claim 33 characterized in that the repositioning mount (50) has a table (510) supported adjustably in height by two rigid stanchions (520, 540) standing on the carriage.

39. The auxiliary table according to claim 38 characterized in that the table is fastened on two elongatable stanchions (520, 540).

40. The auxiliary table according to claim 39 characterized in that each stanchion (520, 540) includes a vertically arranged spindle means (524, 526) coupled by gear means (547, 548) to a common shaft (550), to the laterally outwardly extending end of which is connected a manipulating wheel (530).

41. The auxiliary table according to claim 33 characterized in that the repositioning mount has a table (510) adjustable in height on which two rigid support pedestals (600, 800) are movable lengthwise to the table, each of which is equipped with a supporting ring (650, 850) and a vertical drive and lateral drive for the supporting ring.

42. The auxiliary table according to claim 7 characterized in that the extension plate (68, 88) is adapted for holding additional extension means (900).

* * * * *